United States Patent [19]
Dunstan et al.

[11] Patent Number: 6,087,555
[45] Date of Patent: Jul. 11, 2000

[54] MICE LACKING EXPRESSION OF OSTEOPROTEGERIN

[75] Inventors: Colin Dunstan, Newbury Park; Scott Simonet, Thousand Oaks; Ildiko Sarosi, Newbury Park, all of Calif.

[73] Assignee: Amgen Inc., Thousand Oaks, Calif.

[21] Appl. No.: 08/943,687

[22] Filed: Oct. 15, 1997

[51] Int. Cl.$^7$ .............................. C12N 5/00; C12N 15/00; C12N 15/09; C12N 15/63
[52] U.S. Cl. ................................... 800/18; 800/9; 800/3; 800/21; 800/22; 800/25; 435/320.1; 435/325; 435/455; 435/463
[58] Field of Search .................................. 800/2, 18, 9, 3, 800/21, 22, 25; 536/23.1; 435/320.1, 325, 455, 463

[56] References Cited

FOREIGN PATENT DOCUMENTS

| 0 784 093 | 7/1997 | European Pat. Off. . |
| 0 816 380 | 1/1998 | European Pat. Off. . |
| 97/23614 | 7/1997 | WIPO . |

OTHER PUBLICATIONS

Bucay et al., Genes and Development, vol. 12(9), pp. 1260–1268, May 1, 1998.
Simonet et al. (Cell, 89 (2) 309–19), Apr. 18, 1997.
Rosati et al. (Nature Genetics, 8 (2) 129–35), Oct. 1994.
Levine et al. (Clinical Chemistry, 43 (4) 669–74). Abstract only. Apr. 1997.
Charreau et al. (Transgenic research, 5 (4) 223–34). Abstract only. Jul. 1996.
Engels, et al., Angew. Chem. Int. Ed. Engl., 28:716–734 ((1988).
Boyce et al. J. Clin. Invest. 90:1622–1627 (1992).
Bradley et al. Current Topics in Devel. Biol., 20:357–371 (1986)).
Cappecchi, Science, 244:1288 (1989).
Ebi et al. Blood 75:1247–1251 (1990).
Graves et al. J. Cell. Phys. 145:102–109 (1990).
Grigoriadis et al. Science 266:443–448 (1994).
Hogan et al. *Manipulating the Mouse Embryo: a Laboratory Manual*, Cold Spring Harbor Laboratory Press, Cold Spring Harbor, NY (1986),.
Isozaki et al. Am. J. Path. 145:827–836 (1994).
Johnson et al. Cell 71:577–586 (1992).
Lowe et al. PNAS USA 90:4485–4489 (1993).
Marks et al., J. Heredity 67: 11–18 (1976).
Robertson *Teratocarcinomas and Embryonic Stem Cells: A Practical Approach*, E.J. Robertson, ed. IRL Press, Washington, D.C. (1987).
Sambrook et al *Molecular Cloning: A Laboratory Manual*, cold Spring Harbor Laboratory Press, Cold Spring Harbor, NY (1989).
Shahinian et al., Science, 261:609 (1993).
Silvers The coat colors of mice: A model for mammalian gene action and interaction. Springer–Verlag, New York, (1979).
Soriano et al. Cell 64:693–702 (1991).
Wang et al. Nature 360:741–745 (1992).
Wiktor–Jedrzejczak et al. J.Exp. Med. 156:1516–1527 (1982).
Wiktor–Jedrzejczak et al. PNAS USA 87:4828–4832 (1990).
Yoshida et al. Nature 345:442–444 (1990).
Galli–Tatiadoros et al., Immunological Methods 181: 1–15 (1995).
Karaplis et al., Principles of Bone Biology 1189–1201, Academic Press (1996).
Mizuno et al., Biochem and Biophysical Res. Commun. 247: 610–615 (1998).

*Primary Examiner*—Deborah Crouch
*Assistant Examiner*—Jill D. Martin
*Attorney, Agent, or Firm*—Robert B. Winter; Steven M. Odre; Ron K. Levy

[57] ABSTRACT

Disclosed is a mouse in which expression of the gene encoding Osteoprotegerin is suppressed. Also disclosed is a nucleic acid construct useful in preparing such a mouse, and a cell line containing such construct.

8 Claims, 7 Drawing Sheets

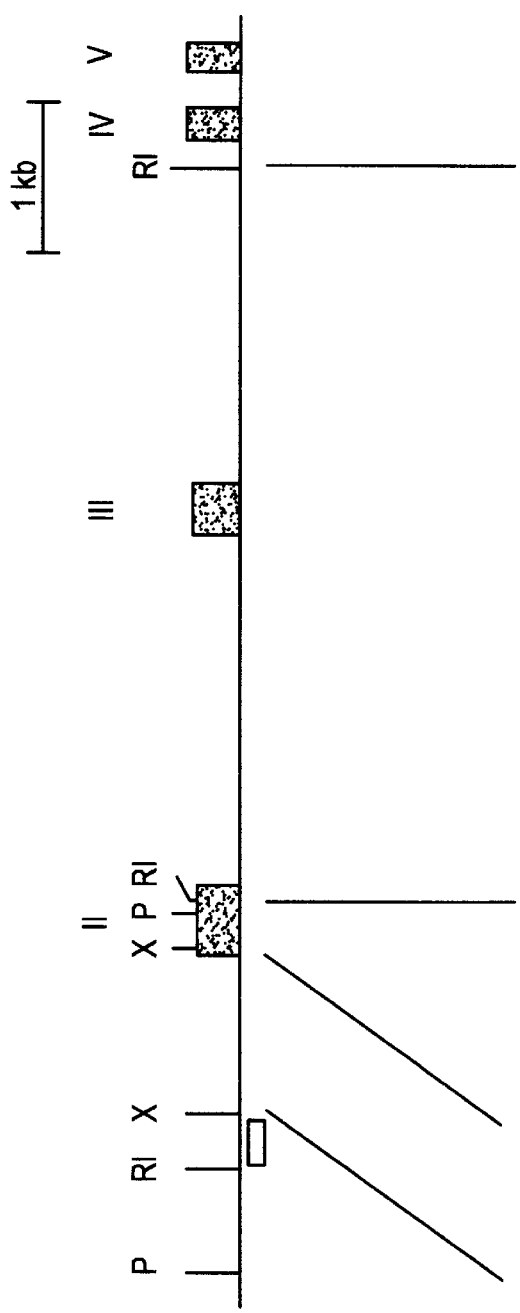
FIG. 1A
FIG. 1B
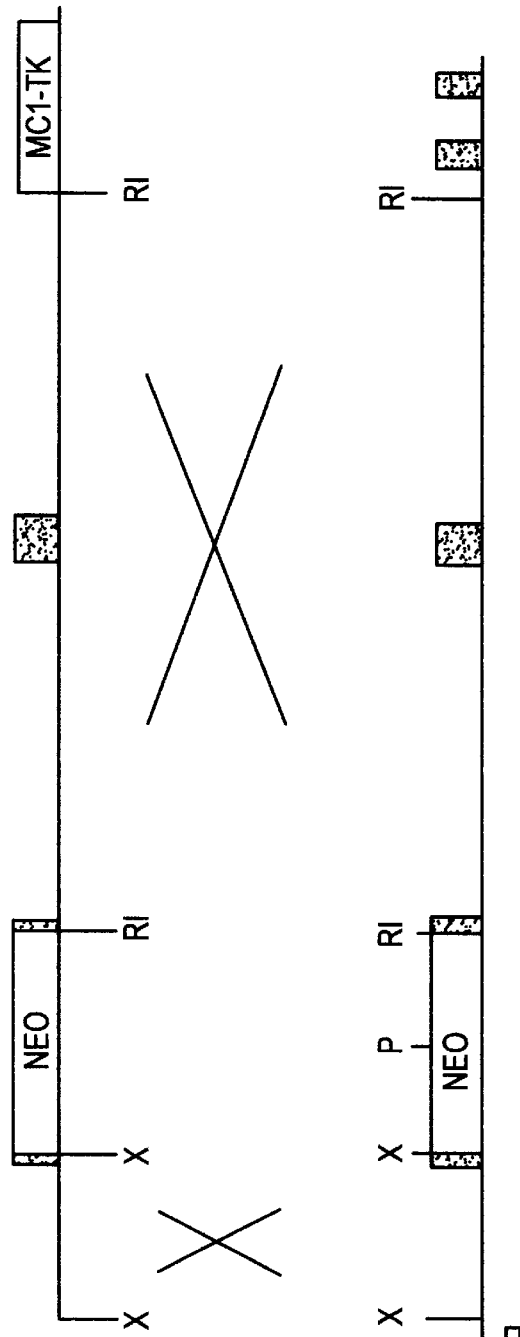
FIG. 1C

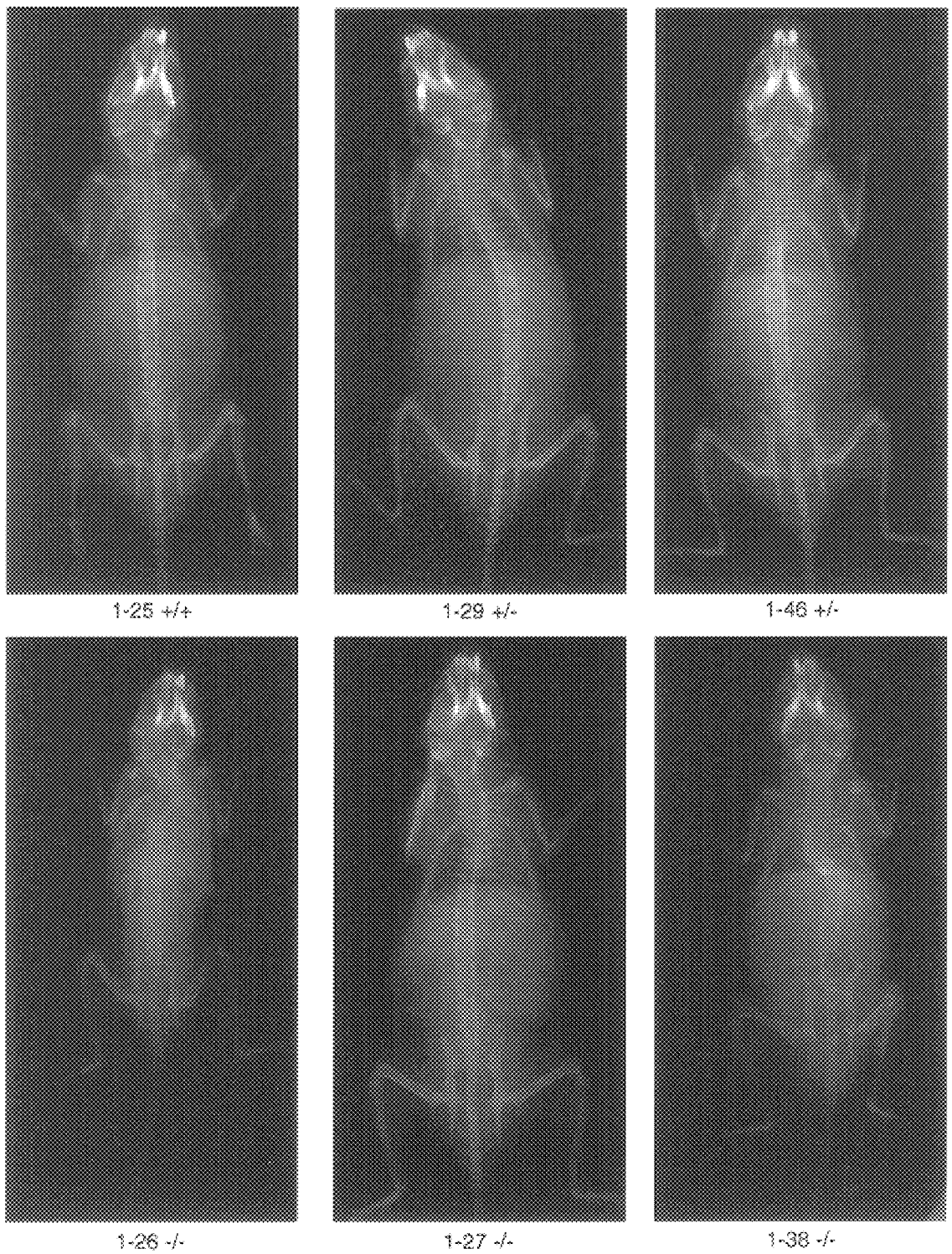

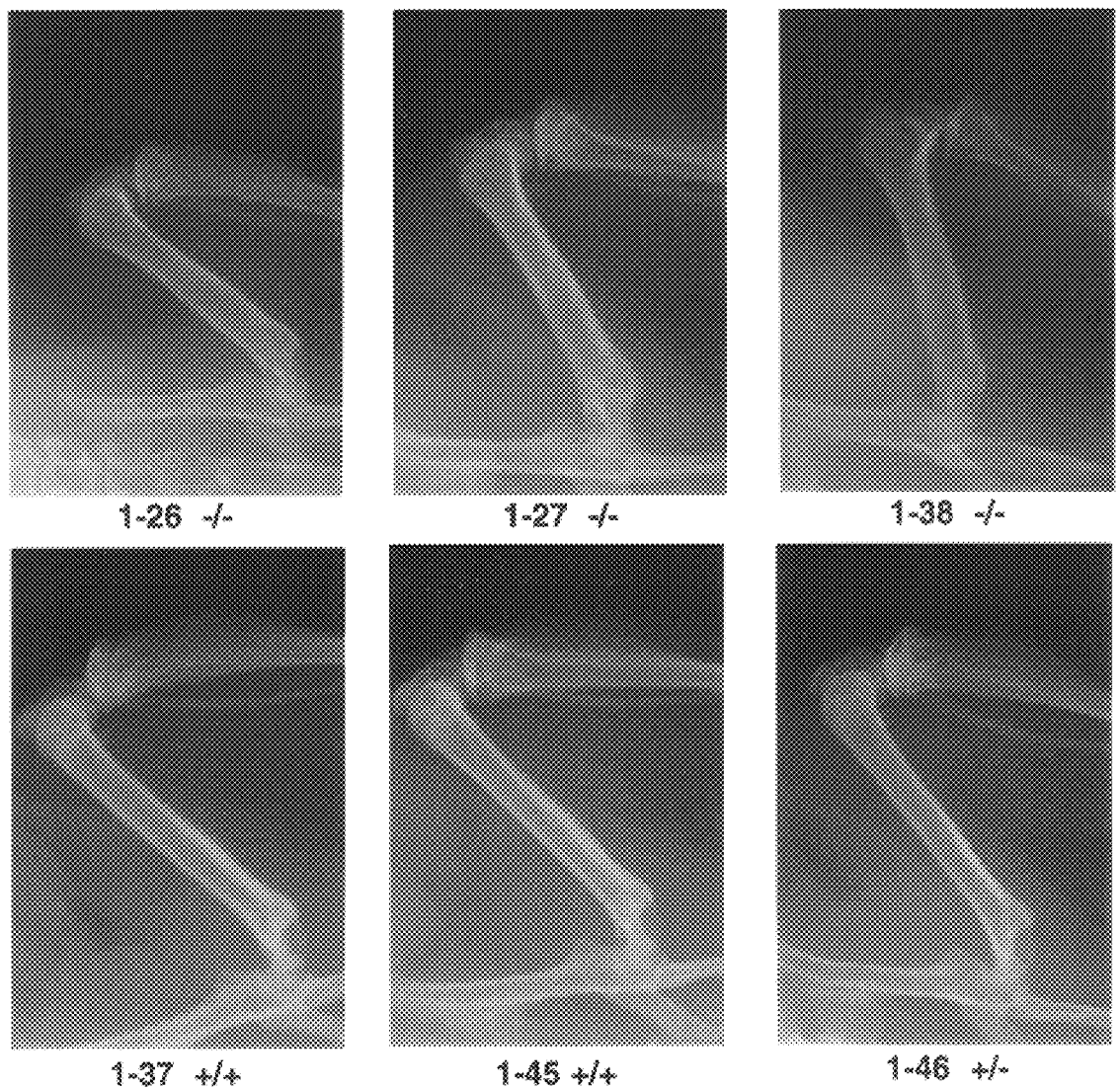

MICE LACKING EXPRESSION OF OSTEOPROTEGERIN

BACKGROUND

1. Field of the Invention

This invention relates to a mammal in which production of the protein encoded by the endogenous gene for osteoprotegerin (OPG) has been completely suppressed.

2. Description of Related Art

Osteoprotegerin (OPG) was recently cloned and characterized as a novel member of the TNFR family that is capable of increasing bone density (Simonet et al. Cell 89, 309–319 (1997) and PCT Application No. US96/20621). By blocking a terminal step in the differentiation and/or activation of osteoclasts from their precursors, OPG is one of several factors with the ability to offset the tight coupling between bone resorption and formation. Administration of recombinant OPG to normal mice or ovariectomized rats results in an increase in bone mass and a decrease in bone resorption. OPG is expressed in cartilage rudiments of developing mouse embryos indicating it may be a physiological regulator of the ossification process.

Overexpression of OPG in transgenic mice resulted in severe osteopetrosis associated with a decrease in osteoclast number and activity in metaphyseal trabecular bone (Simonet et al. supra). The phenotype of OPG transgenic mice differs markedly from other murine models of osteopetrosis. Genetic mutants such as op/op mice (csf- $1^{-/-}$) (Yoshida et al. Nature 345:442–444 (1990); Wiktor-Jedrzejczak et al. Proc. Natl. Acad.Sci. USA 87:4828–4832 (1990); Marks et al. J. Heredity 67:11–18 (1976); Wiktor-Jedrzejczak et al. J.Exp. Med. 156:1516–1527 (1982)), microphthalmic mice (mi/mi) (Ebi et al. Blood 75:1247–1251 (1990), Graves et al. J. Cell. Phys. 145:102–109 (1990); Silvers The coat colors of mice: A model for mammalian gene action and interaction. Springer-Verlag, New York, (1979), Isozaki et al. Am. J. Path. 145:827–836 (1994)), and c-src$^{-/-}$ and c-fos$^{-/-}$ mice (Soriano et al. Cell 64:693–702 (1991), Wang et al. Nature 3:741–745 (1992), Grigoriadis et al. Science 266:443–448 (1994), Johnson et al. Cell 71:577–586 (1992)) all exhibit osteopetrosis accompanied by impaired tooth eruption and retarded growth. The defects in these genetic mutants are generally associated with decreased bone resorption attributable to decreased osteoclast numbers or inactive osteoclasts (Yoshida et al. supra, Wiktor-Jedrzejczak et al., supra; Graves et al., supra; Grigoriadis et al., supra; Boyce et al. J. Clin. Invest. 90:1622–1627 (1992), Lowe et al. Proc. Natl. Acad. Sci. USA 90:4485–4489 (1993)). In general, the long bones of the characterized osteopetrotic mouse models are shortened in length and the mice exhibit modest facial and cranial abnormalities. Osteopetrosis in OPG transgenic founder animals was severe in high expressors, yet occurred without shortening of the long bones or impaired tooth eruption (Simonet et al., supra).

It has been established that pharmacological doses of OPG result in increased bone density. However, there is a need to understand the physiological role of OPG in the development and maintenance of bone mass and other metabolic processes. In particular, there is a need to determine whether OPG is a physiological regulator of bone mass, and whether other factors can compensate to maintain normal bone mass in its absence. Further, an animal model in which bone density is decreased would be valuable for screening novel therapeutics for diseases of bone loss.

Accordingly, it is an object of this invention to provide a mammal in which the gene encoding OPG has been suppressed.

This and other such objects will readily be apparent to one of ordinary skill in the art.

SUMMARY OF THE INVENTION

The invention relates to a mammal in which expression of the gene encoding OPG is suppressed. Also provided is a nucleic acid construct useful in preparing such a mammal, and a cell line containing such a construct.

In one embodiment, the present invention provides a mammal comprising the gene encoding OPG, wherein one allele of the gene has been disrupted. In another embodiment, this invention provides a mammal comprising the gene encoding OPG, wherein both alleles of the gene have been disrupted. In yet another embodiment, this invention provides a mammal comprising a disrupted OPG mutation, wherein the disruption results in a null mutation of the gene encoding OPG.

Preferably, the mammal is a non-human mammal. More preferably, the mammal is a rodent. Optionally, the rodent is a mouse.

In still another embodiment, this invention provides a nucleic acid molecule comprising an OPG knockout construct. Optionally, this construct may be inserted into an amplification and/or an expression vector, and the vector may be useful for transforming a prokaryotic or eukaryotic cell, or an embryo.

In one additional embodiment, the present invention provides a murine RW4 embryonic stem cell line comprising an OPG knockout construct.

Suppression of OPG expression results in a phenotype of decreased bone density and increased bone resorption. The OPG knockout mammals described herein provide a method for screening compounds that modulate bone resorption, and may help identify drugs that treat bone diseases such as osteoporosis.

BRIEF DESCRIPTION OF THE DRAWINGS

FIGS. 1 A–C depicts preparation of an OPG knockout construct. Restriction sites are indicated as follows: "RI" is EcoRI; "X" is XmnI; "P" is PstI. Exons are indicated as black boxes, and introns as thin black lines. (A) depicts a fragment of the OPG native gene containing exons 2–5, part of intron 1 and introns 2–4. (B) depicts the knockout construct in which the thymidine kinase (MC1-TK) cassette and the neomycin (Neo) cassette have been ligated into the OPG gene. (C) Depicts the structure of the targeted allele following homologous recombination at the OPG locus. The small open box represents the probe used to screen for recombinant ES cell clones.

FIG. 4A depicts whole body x-ray of 2 month old wild type (+/+), heterozygous (±), and homozygous (−/−) OPG knockout mice.

FIG. 4B depicts x-rays of the femurs of OPG −/−, +/+ and ± mice. The strongest phenotype is seen in #1–38. The cortical bone is thinned, the growth plate is not visible. The ± mice are not different from the +/+ mice.

DETAILED DESCRIPTION OF THE INVENTION

Figure 2:
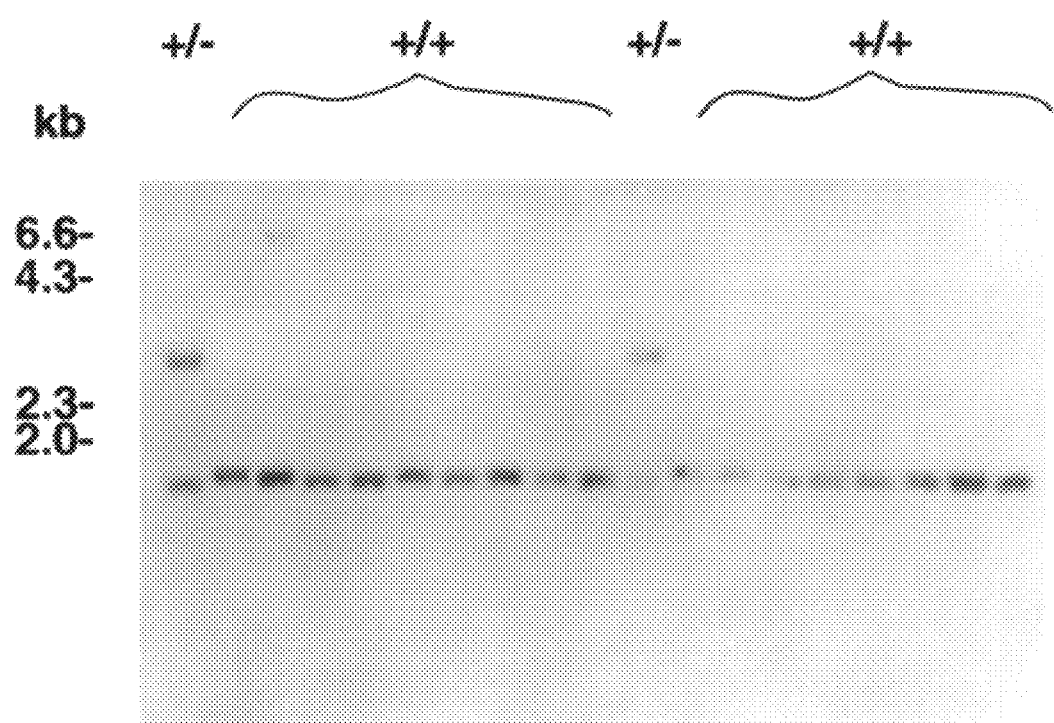
FIG. 2 depicts Southern blot analysis of EcoRI digested genomic DNA from wild type (+/+), or targeted (±) ES cell clones. The wild type allele is a 1.7 kb EcoRI fragment, and the targeted allele is a 3.2 kb EcoRI fragment.

The term "knockout" refers to partial or complete reduction of the expression of at least a portion of a polypeptide encoded by an endogenous gene (such as OPG) of a single cell, selected cells, or all of the cells of a mammal. The mammal may be a "heterozygous knockout", wherein one allele of the endogenous gene has been disrupted. Alternatively, the mammal may be a "homozygous knockout" wherein both alleles of the endogenous gene have been disrupted.

The term "knockout construct" refers to a nucleotide sequence that is designed to decrease or suppress expression of a polypeptide encoded by an endogenous gene in one or more cells of a mammal. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct is inserted into a cell containing the endogenous gene to be knocked out. The knockout construct can then integrate within one or both alleles of the endogenous OPG gene, and such integration of the OPG knockout construct can prevent or interrupt transcription of the full-length endogenous OPG gene. Integration of the OPG knockout construct into the cellular chromosomal DNA is typically accomplished via homologous recombination (i.e., regions of the OPG knockout construct that are homologous or complimentary to endogenous OPG DNA sequences can hybridize to each other when the knockout construct is inserted into the cell; these regions can then recombine so that the knockout construct is incorporated into the corresponding position of the endogenous DNA).

Typically, the knockout construct is inserted into an undifferentiated cell termed an embryonic stem cell (ES cell). ES cells are usually derived from an embryo or blastocyst of the same species as the developing embryo into which it can be introduced, as discussed below.

The phrases "disruption of the gene", "gene disruption", "suppressing expression", and "gene suppression", refer to insertion of an OPG nucleotide sequence knockout construct into a homologous region of the coding region of the endogenous OPG gene (usually containing one or more exons) and/or the promoter region of this gene so as to decrease or prevent expression of the full length OPG molecule in the cell. Insertion is usually accomplished by homologous recombination. By way of example, a nucleotide sequence knockout construct can be prepared by inserting a nucleotide sequence comprising an antibiotic resistance gene into a portion of an isolated nucleotide sequence encoding OPG that is to be disrupted. When this knockout construct is then inserted into an embryonic stem cell ("ES cell"), the construct can integrate into the genomic DNA of at least one OPG allele. Thus, many progeny of the cell will no longer express OPG at least in some cells, or will express it at a decreased level and/or in a truncated form, as at least part of the endogenous coding region of OPG is now disrupted by the antibiotic resistance gene.

The term "marker sequence" refers to a nucleotide sequence that is (1) used as part of a larger nucleotide sequence construct (ie., the "knockout construct") to disrupt the expression of OPG, and (2) used as a means to identify those cells that have incorporated the OPG knockout construct into the chromosomal DNA. The marker sequence may be any sequence that serves these purposes, although typically it will be a sequence encoding a protein that confers a detectable trait on the cell, such as an antibiotic resistance gene or an assayable enzyme not naturally found in the cell. The marker sequence will also typically contain either a homologous or heterologous promoter that regulates its expression.

The terms "rodent" and "rodents" refer to all members of the phylogenetic order Rodentia including any and all progeny of all future generations derived therefrom.

The term "murine" refers to any and all members of the family Muridae, including without limitation, rats and mice.

The term "progeny" refers to any and all future generations derived or descending from a particular mammal, i.e., a mammal containing one or more knockout constructs inserted into its genomic DNA, whether the mammal is heterozygous or homozygous for the knockout construct. Progeny of any successive generation are included herein such that the progeny, the F1, F2, F3, generations and so on indefinitely containing the knockout construct are included in this definition.

Included within the scope of this invention is a mammal in which one or both OPG alleles, as well as one or both alleles of another gene(s), have been knocked out. Such a mammal can be generated by repeating the procedures set forth herein for generating an OPG knockout mammal but using another gene, or by breeding two mammals, one with one or both alleles of OPG knocked out, and one with one or both alleles of a second gene knocked out, to each other, and screening for those offspring that have the double knockout genotype (whether a double heterozygous or a double homozygous knockout genotype, or a variation thereof).

Also included within the scope of this invention is a mammal in which 1) one or both OPG alleles, and optionally one or both alleles of another gene(s), have been knocked out, and 2) one or more transgenes (i.e., exogenous DNA sequence(s) encoding a polypeptide(s) that may or may not be naturally occurring in the mammal) have been inserted.

Knockout Technology

1. Isolation of the OPG Gene

An OPG knockout construct is typically prepared by isolating a portion of the genomic or cDNA OPG nucleotide sequence (usually encoding at least one exon and one intron), and inserting a marker sequence into the OPG sequence. The OPG gene or gene fragment to be used in preparing this construct may be obtained in a variety of ways. Generally, the OPG DNA molecule will be at least about 1 kilobase (kb) in length, and preferably will be 3–4 kb in length, thereby providing sufficient complementary sequence for recognition with chromosomal DNA (i e., homologous recombination) when the knockout construct is introduced into the genomic DNA of the ES cell (discussed below).

A naturally occurring genomic OPG fragment or cDNA molecule to be used in preparing the knockout construct can be obtained using methods well known in the art such as those described by Sambrook et al. (*Molecular Cloning: A Laboratory Manual*, Cold Spring Harbor Laboratory Press, Cold Spring Harbor, N.Y. (1989)). Such methods include, for example, PCR amplification of a particular DNA sequence using oligonucleotide primers, or screening a genomic library prepared from cells or tissues that contain the OPG gene with a cDNA probe encoding at least a portion of the same or a highly homologous OPG gene in order to obtain at least a portion of the OPG genomic sequence. Alternatively, if a cDNA sequence is to be used in a knockout construct, the cDNA may be obtained by screening a cDNA library (preferably one prepared from tissues or that express OPG, where the tissues or cells are derived from the same or a similar species of mammal as that to be rendered the knockout mammal) with oligonucleotide probes, homologous cDNA probes, or antibodies (where the library is cloned into an expression vector). If a promoter sequence is to be used in the knockout construct, synthetic DNA probes or primers can be designed for screening a genomic library or for amplification using PCR, respectively.

Where the DNA sequence of the endogenous OPG gene is known, a DNA fragment encoding the desired portion of such gene may be manufactured synthetically, using chemical synthesis methods such as those described by Engels et al., (Angew. Chem. Int. Ed. Engl., 28:716–734 ((1989)). These methods include inter alia, the phosphotriester, phosphoramidite, and H-phosphonate methods of nucleic acid synthesis. Typically, the genomic DNA fragment to be prepared will be several hundred base pairs in length. Since the chemical synthesis methods set forth herein can be used to make nucleic acid sequences of up to about 100 base pairs, the native genomic DNA can be synthesized in 100 bp fragments which can then be ligated together using standard DNA ligation methods.

The OPG genomic DNA fragment or OPG cDNA molecule prepared for use in the knockout construct must be generated in sufficient quantity for genetic manipulation. Amplification may be conducted by 1) placing the fragment into a suitable vector and transforming bacterial or other cells that can rapidly amplify the vector, 2) by PCR amplification, 3) by synthesis with a DNA synthesizer, or 4) by other suitable methods.

2. Preparation of an OPG Knockout Construct

The OPG genomic DNA fragment, cDNA molecule, or PCR fragment to be used in making the OPG knockout construct can be digested with one or more restriction enzymes selected to cut at a location(s) such that a second DNA molecule encoding a marker gene can be inserted in the proper position within the OPG genomic DNA fragment, cDNA molecule, or PCR fragment to be used in the construct. The proper position for marker gene insertion is one that will serve to decrease or prevent transcription and/or expression of the full length endogenous OPG gene. This position will depend on various factors such as the available restriction sites in the sequence to be cut, whether an exon sequence or a promoter sequence, or both is (are) to be interrupted, and whether several isoforms of OPG exist in the mammal (due to alternative splicing) and only one such isoform is to be disrupted. Preferably, the enzyme(s) selected for cutting the OPG genomic DNA, cDNA molecule, or PCR fragment will generate a longer arm and a shorter arm, where the shorter arm is at least about 300 base pairs (bp). In some cases, it will be desirable to actually delete a portion or even all of one or more introns or exons of this native genomic or cDNA molecule. In these cases, the OPG genomic DNA, cDNA molecule, or PCR fragment can be cut with appropriate restriction endonucleases such that a fragment of the proper size and proper location can be removed.

The marker gene used in the knockout construct can be any nucleic acid molecule that is detectable and/or assayable after it has been incorporated into the genomic DNA of the ES cell, and ultimately the knockout mammal, however typically it is an antibiotic resistance gene or other gene whose expression or presence in the genome can easily be detected. Preferably, the marker gene encodes a polypeptide that does not naturally occur in the mammal. The marker gene is usually operably linked to its own promoter or to another strong promoter such as the thymidine kinase (TK) promoter or the phosphoglycerol kinase (PGK) promoter from any source that will be active or can easily be activated in the cell into which it is inserted; however, the marker gene need not have its own promoter attached, as it may be transcribed using the promoter of the gene to be knocked out. In addition, the marker gene will normally have a polyA sequence attached to its 3' end; this sequence serves to terminate transcription of the marker gene. Preferred marker genes are any antibiotic resistance gene such as neo (the neomycin resistance gene) and beta-gal (beta-galactosidase).

After the OPG genomic DNA fragment, cDNA molecule, or PCR fragment has been digested with the appropriate restriction enzyme(s), the marker gene molecule can be ligated with the native genomic DNA or cDNA molecule using methods well known to the skilled artisan and described in Sambrook et al., supra. In some cases, it will be preferable to insert the marker sequence in the reverse or antisense orientation with respect to the OPG nucleic acid sequence; this reverse insertion is preferred where the marker gene is operably linked to a particularly strong promoter.

The ends of the DNA molecules to be ligated must be compatible; this can be achieved by either cutting all fragments with those enzymes that generate compatible ends, or by blunting the ends prior to ligation. Blunting can be done using methods well known in the art, such as for example by the use of Klenow fragment (DNA polymerase I) to fill in sticky ends. After ligation, the ligated constructs can be screened by selective restriction endonuclease digestion to determine which constructs contain the marker sequence in the desired orientation.

The ligated DNA knockout construct may be transfected directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

3. Transfection of Embryonic Stem Cells

The OPG knockout construct is typically transfected into stem cells derived from an embryo (embryonic stem cells, or "ES cells") ES cells are undifferentiated cells that are capable of taking up extra-chromosomal DNA and incorporating it into their chromosomal DNA. Generally, the ES cells used to produce the knockout mammal will be of the same species as the knockout mammal to be generated. Thus for example, mouse embryonic stem cells will usually be used for generation of knockout mice.

The embryonic stem cell line used is typically selected for its ability to integrate into and become part of the germ line of a developing embryo so as to create germ line transmission of the knockout construct. Thus, any ES cell line that is believed to have this capability is suitable for use herein. Preferred ES cell lines for generating knockout mice are murine cell lines D3 and E14 (American Type Culture Collection, 12301 Parklawn Drive, Rockville, Md. 20852-1776 USA, catalog nos. CRL 1934 and CRL 1821, respectively), or RW4 (Genome Systems, Inc., 8620 Pennell Drive, St. Louis, Mich. 63114 USA, catalog No. ESVJ-1182). The cells are cultured and prepared for DNA insertion using methods well known to the skilled artisan such as those set forth by Robertson (in: *Teratocarcinomas and Embryonic Stem Cells: A Practical Approach*, E. J. Robertson, ed. IRL Press, Washington, D.C. (1987)), by Bradley et al. (Current Topics in Devel. Biol., 20:357–371 (1986)) and by Hogan et al. (*Manipulating the Mouse Embryo: A Laboratory Manual*, Cold Spring Harbor Laboratory Press, Cold Spring Harbor, N.Y. (1986)).

Insertion (also termed "transfection") of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

The OPG knockout construct DNA molecules to be transfected into the cells can first be linearized if the knockout construct has previously been inserted into a circular vector. Linearization can be accomplished by digesting the DNA with a suitable restriction endonuclease selected to cut only within the vector sequence and not within the knockout construct sequence.

The isolated OPG knockout construct DNA can be added to the ES cells under appropriate conditions for the insertion method chosen. Where more than one construct is to be introduced into the ES cells, the DNA molecules encoding each construct can be introduced simultaneously or sequentially. Optionally, homozygous OPG knockout ES cells may be generated by adding excessive OPG knockout construct DNA to the cells, or by conducting successive rounds of transfection in an attempt to achieve homologous recombination of the knockout construct on both endogenous OPG alleles.

If the ES cells are to be electroporated, the ES cells and knockout construct DNA are exposed to an electric pulse using an electroporation machine and following the manufacturer's guidelines for use. After electroporation, the cells are typically allowed to recover under suitable incubation conditions. The cells are then screened for the presence of the knockout construct.

Screening the ES cells can be accomplished using a variety of methods, but typically, one screens for the presence of the marker sequence portion of the knockout construct. Where the marker gene is an antibiotic resistance gene, the cells can be cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. If the marker gene is a gene that encodes an enzyme whose activity can be detected (e.g., beta-galactosidase), the enzyme substrate can be added to the cells under suitable conditions, and the enzymatic activity of the marker gene can be analyzed.

The knockout construct may integrate into several locations in the ES cell genome, and may integrate into a different location in each cell's genome, due to the occurrence of random insertion events; the desired location of insertion is within the OPG endogenous gene sequence. Typically, less than about 1–10 percent of the ES cells that take up the knockout construct will actually integrate the knockout construct in the desired location. To identify those cells with proper integration of the knockout construct, chromosomal DNA can be extracted from the cells using standard methods such as those described by Sambrook et al., supra. This DNA can then be probed on a Southern blot with a probe or probes designed to hybridize to the knockout construct DNA digested with (a) particular restriction enzyme(s). Alternatively, or additionally, a specific genomic DNA sequence can be amplified by PCR with probes specifically designed to amplify that DNA sequence such that only those cells containing the knockout construct in the proper position will generate DNA fragments of the proper size.

4. ES Cell Incorporation/Implantation of Embryos

After suitable ES cells containing the knockout construct in the proper location have been identified, the cells can be incorporated into an embryo. Incorporation may be accomplished in a variety of ways. A preferred method of incorporation of ES cells is by microinjection into an embryo that is at the blastocyst stage of development. For microinjection, about 10–30 cells are collected into a micropipet and injected into a blastocyst to integrate the ES cell into the developing blastocyst.

The suitable stage of development for the blastocyst is species dependent, however for mice it is about 3.5 days. The blastocysts can be obtained by perfusing the uterus of pregnant females. Suitable methods for accomplishing this are known to the skilled artisan, and are set forth for example by Bradley (in Robertson, ed., supra).

While any blastocyst of the right age/stage of development is suitable for use, preferred blastocysts are male and have genes coding for a coat color or other phenotypic marker that is different from the coat color or other phenotypic marker encoded by the ES cell genes. In this way, the offspring can be screened easily for the presence of the knockout construct by looking for mosaic coat color or other phenotypic marker (indicating that the ES cell was incorporated into the developing embryo). Thus, for example, if the ES cell line carries the genes for white fur, the embryo selected will preferably carry genes for black or brown fur.

An alternate method of preparing an embryo containing ES cells that possess the knockout construct is to generate "aggregation chimeras". A morula of the proper developmental stage (about 2½ days old for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morula and ES cells.

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extraembryonic membrane. Therefore, when ES cells are co-cultured with the zygotic cells, the developing embryo is comprised exclusively of ES cells.

After the ES cells have been incorporated, the aggregation chimera or transfected embryo can be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2–3 days pseudopregnant.

5. Screening for the OPG Knockout Gene

Offspring that are born to the foster mother may be screened initially for mosaic coat color or other phenotype marker where the phenotype selection strategy (such as coat color, as described above) has been employed. In addition, or as an alternative, chromosomal DNA obtained from tail tissue of the offspring may be screened for the presence of the knockout construct using Southern blots and/or PCR as described above. The offspring that are positive for the OPG knockout construct will typically be heterozygous, although some homozygous knockouts may exist, and can typically be detected by visually quantifying the amount of probe that hybridizes to the Southern blots.

If homozygous knockout mammals are desired, they can be prepared by crossing those heterozygous offspring believed to carry the knockout construct in their germ line to each other; such crosses may generate homozygous knockout animals. If it is unclear whether the offspring will have germ line transmission, they can be crossed with a parental or other strain and the offspring screened for heterozygosity. Homozygotes may be identified by Southern blotting of equivalent amounts of genomic DNA from mammals that are the product of this cross, as well as mammals of the same species that are known heterozygotes, and wild-type mammals. Probes to screen the Southern blots for the presence of the knockout construct in the genomic DNA can be designed as set forth above.

Other means of identifying and characterizing the knockout offspring are also available. For example, Northern blots can be used to probe mRNA obtained from various tissues of the offspring for the presence or absence of transcripts encoding either the gene knocked out, the marker gene, or both. In addition, Western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Both the heterozygous and homozygous OPG knockout mammals of this invention will have a variety of uses, since OPG has been implicated in regulation of differentiation and activation of osteoclasts. One such use will be to use the mammal as an in vivo screening system for drugs that affect bone resorption. It is known that osteoclast numbers increase in certain bone diseases, as well as in response to certain cytokines or hormones (i.e., interleukin-1 (IL-1) or parathyroid hormone (PTH)) that stimulate bone resorption. In addition, certain diseases such as osteoporosis generally result in imbalances between bone resorption and bone formation. As such, the claimed mammals may be used to screen for drugs useful for altering osteoclast numbers and/or activity, i.e., drugs that either enhance or inhibit these activities, depending on the disease under study.

Screening for such useful drugs typically involves administering the candidate drug over a range of doses to the mammal, and assaying at various time points for the bone density effect(s) of the drug on the disorder being evaluated. Such assays would include, for example, looking for increased or decreased osteoclast numbers, increased or decreased bone resorption, increased or decreased bone production and/or density, increased or decreased levels and/or activity of chemical messengers such as interleukins, and/or increased or decreased levels of expression of a particular gene(s) involved in the modulation of bone density.

For example, patients with osteoporosis often experience bone fractures. It would be desirable to block osteoclast-mediated bone resorption in such individuals by administering to the patient a therapeutic agent capable of producing such an effect. A mammal of the present invention could be used to screen a variety of compounds, either alone or in combination, to determine whether partial or total inhibition of osteoclast-mediated bone resorption results from the use of such drug.

The same strategy could be applied to find compounds that would be useful in suppressing bone resorption in patients with other diseases of bone loss, such as hypercalcemia of malignancy or in patients with disorders of bone remodeling, such as Paget's disease.

In addition, a mammal of the present invention can be useful for evaluating the development and function of various components of the skeletal system, and for studying the effects of particular gene mutations. For example, in a mammal not expressing OPG, one can analyze the effect of the lack of such expression on other components of the skeletal system.

Other uses of the claimed mammals and compounds will be readily apparent to one of skill in the art.

The invention will be more fully understood by reference to the following examples. These examples are not to be construed in any way as limiting the scope of this invention.

EXAMPLES

Example 1

Preparation of an OPG Knockout Construct

To obtain murine OPG genomic DNA clones, a 129 SVJ Mouse genomic library in Lambda Fix II Vector (Stratagene, Inc., 11011 North Torrey Pines Road, La Jolla, Calif. 92037, catalog No. 946309) was screened with a radiolabeled DNA fragment corresponding to nucleotides 90–1296 of the murine OPG cDNA (Genbank accession No. U94331). Eleven clones were obtained when the library was screened at a stringency of about 55° C. in about 40 mM sodium phosphate, pH 7.4. These clones were further subdivided by screening with cDNA fragments from the 5'and 3'ends of the coding sequence. The 5'clones were analyzed by Southern blot analysis following digestion with EcoRI.

Recovery of the cloned sequences and plasmid amplification was conducted using LambdaSorb Phage Adsorbent™ (Promega, Inc., 2800 Woods Hollow Road, Madison, Wis. 53711-5399 USA, catalog # A7051) according to the manufacturer's protocol. One clone (fragment 1) was then prepared as a EcoRI/EcoRI fragment and was approximately 1.7 kb. A second clone was prepared as a EcoRI/EcoRI fragment (fragment 2) and was about 5.5 kb in length. Fragment 1 contained a portion of intron 1 and most of exon 2 (see FIG. 1) and fragment 2 contained the 3'portion of exon 2, intron 2, exon 3, and most of intron 3 (see FIG. 1). A third clone prepared as a 1.1 kb XmnI/XmnI fragment (fragment 3) was derived as a subfragment of fragment 1 (see FIG. 1). Fragments 2 and 3, along with a neo cassette containing a PGK (phosphoglycerate kinase) promoter derived from the pKJ-1 vector (Tybutewicz et al., Cell, 65:1153–1163 (1991); Adra et al., Gene, 60:65–74 (1987)) and a TK cassette (thymidine kinase gene with a PGK promoter; Tybutewicz et al., supra) were directionally cloned, using standard ligation techniques, into the vector pBluescript (Stratagene, La Jolla, Calif.) to generate a knockout construct containing, from 5' to 3', OPG genomic fragment 3, the neo cassette, OPG genomic fragment 2, and the TK (see FIG. 1). Both the TK cassette and the neo cassette were ligated in the antisense direction. To confirm proper ligation, the cloning junctions were sequenced.

This vector, containing all components in the proper orientation, was linearized with NotI and then electroporated into RW4 embryonic stem cells as follows: about 25 μg of linearized DNA was added to about $9 \times 10^6$ ES cells in a volume of about 900 μl of PBS. The cells were pulsed at about 0.23 kilovolts and about 500 μF, and each vial of cells was then plated onto two 60 mm cell culture plates with feeder cells. The plates contained about 10 ml of DMEM medium (Gibco/BRL, Grand Island, N.Y.), 15 percent fetal calf serum (Gibco/BRL, Grand Island, N.Y. or equivalent from Hyclone Labs, Logan, Utah), and leukemia inhibitory factor (Fung-Leung et al. Cell, 65:443–449 (1991)), $10^{-5}$ M B-mercaptoethanol, 2 mM L-glutamine, and 1 mM sodium pyruvate. After two days in culture, the cells were selected in the presence of gangcyclovir and G418 to enrich for cells which had undergone homologous recombination (Cappecchi, Science, 244:1288 [1989]; Shahinian et al., Science, 261:609 (1993)); surviving cells were collected, and cultured further in medium containing G418 but not gangcyclovir. To confirm homologous recombination, the cells that grew in the presence of G418 were then screened by Southern blot analysis using genomic DNA prepared from the cells and cut with EcoRI (see FIG. 2).

Samples of RW4 cells that have undergone homologous recombination to incorporate the OPG knockout construct in their genomic DNA have been deposited with the American Type Culture Collection ("ATCC", 12301 Parklawn Drive, Rockville, Md. 20852, USA) as accession number CRL-12418, with a deposit date of Oct. 9, 1997.

Example 2

Preparation of OPG Knockout Mice

Figure 3:
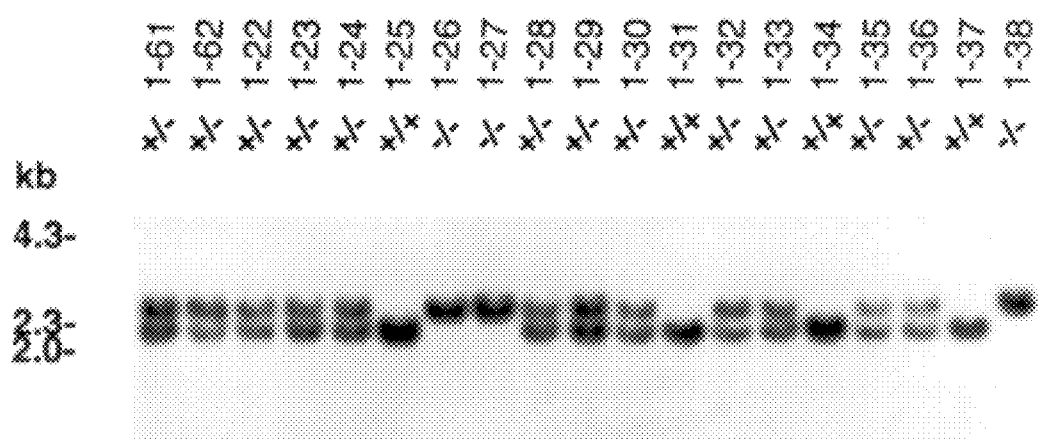
FIG. 3 depicts Southern blot analysis of PstI digested genomic DNA from wild type (+/+), heterozygous (±), and homozygous (−/−) OPG knockout mice. The wild type allele is a 2.3 kb PstI fragment, and the targeted allele is a 3.0 kb PstI fragment.

The RW4 cells containing the OPG knockout construct were inserted into fertilized embryos (blastocysts) that were approximately 3.5 days old, which were obtained from C57BL/6 mice by perfusing the uterus of female C57BL/6 mice that had been mated with male mice. Insertion was accomplished by microinjecting about 15–30 cells into each blastocyst. The embryos were then implanted into CD1 pseudo pregnant female mice at day 2.5 post coitum for gestation. The chimeric male offspring of these foster mothers were screened for agouti coat color and were crossed with female C57BL/6 or swiss black females. Germline transmission of the knockout construct was determined by coat color of the $F_1$ pups; agouti pups were identified as heterozygous OPG knockouts. These $F_1$ pups were crossed with each other to generate $F_2$ homozygotes. The homozygotes (OPG$^{-/-}$) were identified and distinguished from heterozygotes (OPG$^{+/-}$) and wildtype (OPG$^{+/+}$) mice by Southern blot analysis of genomic DNA cut with PstI and probed with a EcoRI/XmnI OPG specific probe which was used to confirm homologous recombination (see FIG. 3).

Example 3

Characterization of OPG Knockout Mice

The following procedures were used for all analyses described below in which qualitative and/or quantitative phenotypic analysis of bone and other tissues of OPG knockout and control mice was performed. At 8–10 weeks of age, 3 homozygous OPG knockout mice (OPG$^{-/-}$), 5 heterozygous OPG knockout mice (OPG$^{+/-}$) and 4 control mice (OPG$^{+/+}$) were necropsied (see Table 1). Radiography was performed prior to the gross dissection. Serum from the mice was analyzed for clinical chemistries and full hematology. Total body and major organs were weighed and fixed in formalin. Tibias for pQCT measurements were fixed in 70% ETOH. The bone density in the proximal tibial metaphysis and tibial cortical shaft of wild type, heterozygous, and OPG$^{-/-}$ mice was determined by quantitative CT scanning (pQCT) (Stratec, Germany). Two standard slices of bone, 0.5 mm in thickness 1.5 mm from the proximal end and a single 0.5 mm slice 4 mm from the proximal end of the tibia were used to determine the trabecular bone density in the metaphysis and the mineral content and density of the cortical shaft respectively. Other bone tissue was decalcified using a formic acid solution, and all sections were stained with H & E. Enzyme histochemistry was performed to determine the expression of expression of tartarate resistant acidic phosphatase (TRAP). Seven additional OPG$^{-/-}$ mice between 8 and 16 weeks of age were bled for serum chemistries. These mice were designated 1-51, 1-56, 1-68, 1-74, 1-83, 4-78 and 4-79.

TABLE 1

| Knockout Mice Undergoing Necropsy | | |
|---|---|---|
| OPG (+/+) | OPG (+/-) | OPG (-/-) |
| 1-34 | 1-28 | 1-27 |
| 1-37 | 1-29 | 1-26 ◆ |
| 1-45 | 1-35 | 1-38 ▼ |
| 1-25 | 1-36 | |
| | 1-46 | |

◆ OPG$^{-/-}$ Mouse 1-26 was the runt of the litter, about half the size of a normal mouse. It became moribund and died shortly before the scheduled sacrifice, it displayed the signs of respiratory insufficiency shortly before dying. Blood for hematology and serum chemistries was drawn immediately after death by cardiac puncture and a regular necropsy was performed.
▼ OPG$^{-/-}$ Mouse 1-38 was placed in one cage with OPG-/- mouse 1-27 in preparation for the procedures and died within the last 1 hour prior to sacrifice, no blood could be collected for testing. The rest of the autopsy was performed as usual and organs submitted for histology.

Pathological evaluation of 8–10 week old OPG wild type, heterozygous knockout and homozygous knockout mice indicated that all three homozygous (OPG$^{-/-}$) knockout mice have severe osteoporosis. The OPG$^{-/-}$ mice were x-rayed adjacent to wild type and/or heterozygous mice using the same x-ray film, to allow direct comparison of bone density and structure (see FIG. 4a). The three OPG$^{-/-}$ mice varied markedly in size with 27 and 38 being of similar size to wild type mice and 26 being profoundly runted. The thoracic vertebrae of mouse 38 were clearly displaced indicating spinal fracture as the cause of death.

There were several consistent differences between the radiological appearance of the bones in the knockout mice compared to those in wild type and heterozygote mice. The most clearly different region was the distal femur (see FIG. 4b). In the distal femoral metaphysis there was a marked reduction in density that was particularly severe in 38 and 26 and less severe in 27. In particular the clear radiodense outlining of the growth plate seen in wild type and heterozygous mice was absent in all knockout mice. The cortical bone of the femur appeared thin in 38 and 26 and in all knockout mice the radiodensity of the cortical bone was decreased. There was also an apparent flattening of the normally rounded distal end of the femur possibly indicating partial collapse or compression of the distal femoral epiphysis. In the proximal end of the tibia there was a loss of a clearly defined growth plate. In the vertebra there was also a reduction in bone density relative to wild type mice with a reduction greatest in 26 and 38 and least in 27.

Figure 5A:
FIGS. 5 A–H depicts bone morphology in OPG -/- (#38) versus normal control (#45) mouse. A—normal control humerus (#45), H & E, size bar 500 microns, note normal morphology; B—OPG -/- humerus (#38), H & E, size bar 500 microns, note severe osteoporosis and mechanical damage of the articular surface; C—normal control vertebra (#45), H & E, size bar 500 microns, note normal morphology; D—OPG -/- vertebra (#38), H & E, size bar 500 microns, note severe osteoporosis and degenerative damage of the intervertebral disk; E—normal control humerus (#45), H & E, size bar 100 microns, note normal morphology; F—OPG -/- humerus (#38), H & E, size bar 100 microns, note severe osteoporosis, increased porosity in the cortical bone; G—normal control vertebra (#45), TRAP stain, size bar 25 microns, note normal number of osteoclasts (arrow); H—OPG -/- vertebra (#38), TRAP stain, size bar 25 microns, note slightly increased number of osteoclasts (arrows).
Figure 5B:
Figure 5C:
Figure 5D:
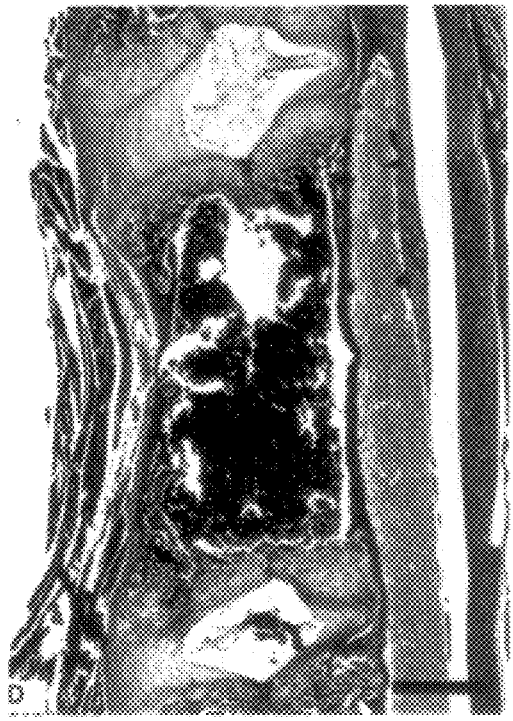
Figure 5E:
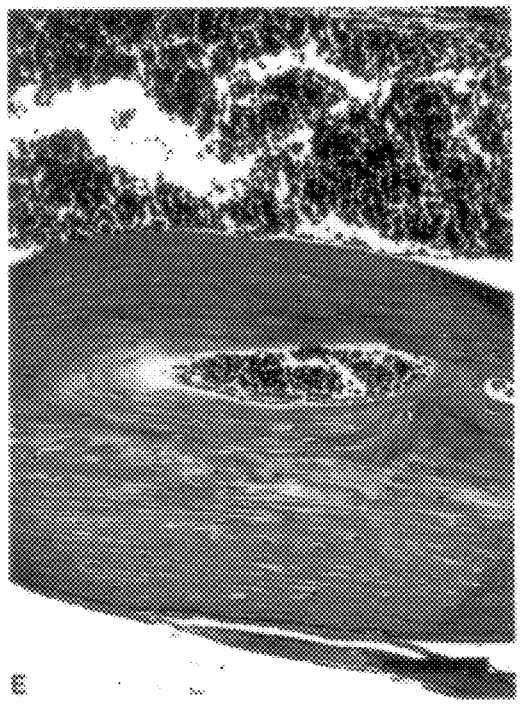
Figure 5F:
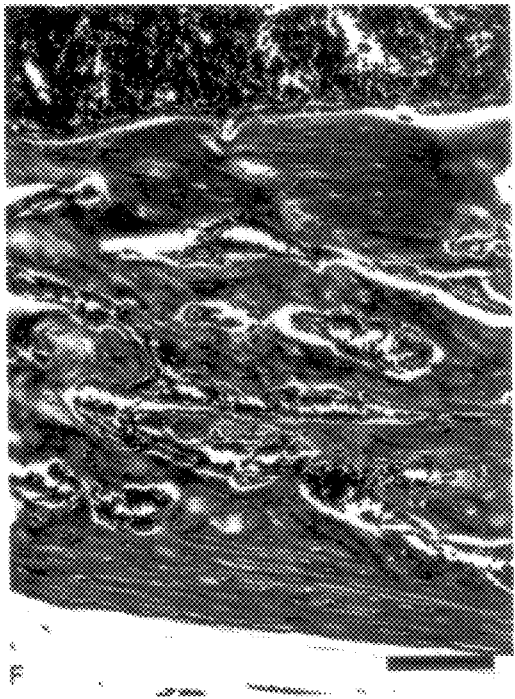

Histologic morphology of OPG knockout mice was also assessed. The lumbar vertebrae and proximal metaphyseal region of the humerus were profoundly osteoporotic with almost complete absence of trabeculae (see FIGS. 5A, B, C, D). The cortical shafts of the humerus in these bones showed increased cortical porosity with the presence of very active remodeling of the cortical bone as evidenced by plentiful osteoclasts and osteoblasts (FIGS. 5E, F). Cortical bone in wild type mice had few cavities or vascular channels and showed little evidence of remodeling (FIG. 5E) whereas in the $OPG^{-/-}$ mice extensive cortical bone porosity was present (FIG. 5F). In the proximal epiphysis of the $OPG^{-/-}$ mice there was evidence of resorption of the subchondral bone and collapse of the joint surface with increased remodeling of the trabecular bone (FIG. 5B).

The trabecular bone density was markedly reduced in the metaphyseal region (268.5±0.16 mg/cm$^3$ versus 443.8±27 mg/cm$^3$ in the heterozygotes and 473.4±30 mg/cm$^3$ in the wild type group). The bone mineral content (0.526 mg/cm$^3$ versus 0.9±0.11 mg/cm$^3$ in the heterozygotes and 0.86±0.2 mg/cm$^3$ in the wild type), and cortical thickness were significantly reduced (to 0.23±0.03 mm from 0.3±0.04 mm in the wild type and 0.32±0.03 mm in the heterozygote group) and cortical density was markedly but not statistically significantly reduced in the tibial cortical shaft.

Figure 5G:
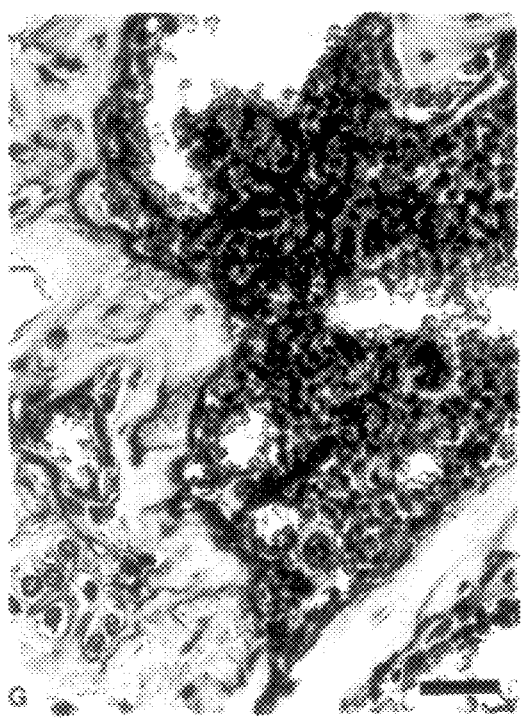
Figure 5H:
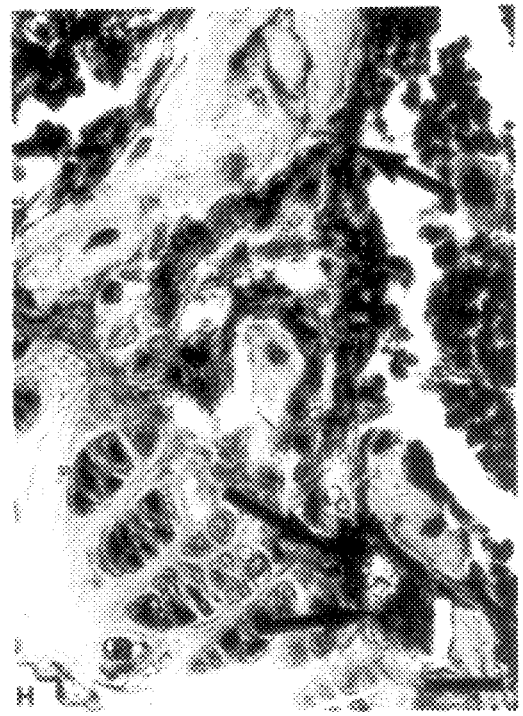

Histomorphometry of the vertebrae and humerus revealed that the trabecular bone volume in the proximal metaphysis of the humerus is significantly reduced (6.58±1.9% versus 21.66±8.6% in the wild type group), and the number of osteoclasts per mm of trabecular bone perimeter was significantly increased (4.88±1.19 versus 3.2±0.25 in the wild type group). In the vertebra similar changes in the trabecular bone volume were recorded, however osteoclast numbers were similar in the $OPG^{-/-}$ and wild type mice (FIG. 5G and H).

No hematology parameters were different between the $OPG^{+/+}$ and $OPG^{+/-}$ groups. $OPG^{-/-}$ mouse 27 was no different from the previous groups, runt #26 had elevated hematocrit, white blood cell count, white blood cell, red blood cell, lymphocyte, monocyte and eosinophil counts due to terminal hemoconcentration. Blood was not available for analysis from #38.

Most chemistry values were normal and similar throughout the groups. Runt #26 had elevated serum calcium and serum cholesterol levels and severely decreased serum glucose. However, all $OPG^{-/-}$ mice, including the seven examined on the additional bleed had elevated serum alkaline phosphatase (ALP) levels. On pooled analysis of the blood chemistry data of the sacrificed and the additionally bled OPG knockouts, the $OPG^{-/-}$ mice had ALP values of 376.3±36.6 IU/1 versus 115.7±55 IU/1 in the $OPG^{+/-}$ and 116.4±36.6 IU/1 in the $OPG^{+/-}$ mice (p<0.001).

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A transgenic mouse whose genome comprises a disruption of the endogenous osteoprotegerin (OPG) gene, wherein said disruption comprises the insertion of a selectable marker sequence, and wherein said disruption results in said mouse exhibiting decreased bone density as compared to a wild-type mouse.

2. The transgenic mouse of claim 1, wherein said disruption is a homozygous disruption.

3. The transgenic mouse of claim 2, wherein said homozygous disruption results in a null mutation of the endogenous gene encoding osteoprotegerin (OPG).

4. An isolated nucleic acid comprising an osteoprotegerin (OPG) knockout construct comprising a selectable marker sequence flanked by DNA sequences homologous to the endogenous OPG gene, wherein when said construct is introduced into a mouse or an ancestor of said mouse at an embryonic stage, said selectable marker sequence disrupts the endogenous OPG gene in the genome of said mouse such that said mouse exhibits decreased bone density as compared to a wild type mouse.

5. A vector comprising the nucleic acid of claim 4.

6. A mouse RW4 embryonic stem cell line comprising the osteoprotegerin (OPG) knockout construct of claim 4.

7. A method of screening compounds that modulate bone resorption comprising introducing a compound into the mouse of claim 1 and determining the increase or decrease in bone resorption of said mouse as compared to the bone resorption of said mouse prior to the administration of the compound.

8. The osteoprotegerin (OPG) knockout construct according to claim 4, wherein said construct comprises from 5' to 3', the OPG genomic fragment 3 which is a XmnI/XmnI subfragment of a portion of exon 1 and most of exon 2, the neo cassette, OPG genomic fragment 2 which is an EcoRI/EcoRI fragment of the 3' portion of exon 2, intron 2, extron 3, and most of intron 3, and the thymidine kinase cassette.

* * * * *